(12) United States Patent
Childers et al.

(10) Patent No.: US 7,026,320 B2
(45) Date of Patent: Apr. 11, 2006

(54) SEROTONERGIC AGENTS

(75) Inventors: Wayne E. Childers, New Hope, PA (US); Michael G. Kelly, Thousand Oaks, CA (US); Sharon J. Rosenzweig-Lipson, East Brunswick, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/441,536

(22) Filed: May 20, 2003

(65) Prior Publication Data

US 2003/0216408 A1 Nov. 20, 2003

Related U.S. Application Data

(63) Continuation of application No. 10/218,251, filed on Aug. 14, 2002, now Pat. No. 6,586,436, which is a continuation of application No. 10/010,575, filed on Nov. 13, 2001, now Pat. No. 6,469,007.

(60) Provisional application No. 60/297,814, filed on Jun. 13, 2001, provisional application No. 60/253,301, filed on Nov. 28, 2000.

(51) Int. Cl.
*A61K 31/496* (2006.01)
(52) U.S. Cl. .................................. 514/253.11; 544/364
(58) Field of Classification Search ............ 514/253.11
See application file for complete search history.

(56) References Cited

U.S. PATENT DOCUMENTS 6,127,357 A 10/2000 Cliffe et al.

FOREIGN PATENT DOCUMENTS

WO WO 97/03982 2/1997

OTHER PUBLICATIONS

Jones et al. Pharmacology Biochemistry and Behavior 71,p. 555-568 (2002).*
Albert J. Robichaud et al., Annual Reports in Med. Chem., Nov. 20, 2000, 35.
B.J. Van Steen et al., J. Med. Chem., 1994, 2761-2773, 37.

* cited by examiner

*Primary Examiner*—Emily Bernhardt
(74) *Attorney, Agent, or Firm*—Wilmer Cutler Pickering Hale & Dorr, LLP

(57) ABSTRACT

Novel piperazine derivatives are provided having the formula (III)

wherein $R_1$ is cyano, nitro, trifluoromethyl or halogen, or pharmaceutically acceptable acid addition salts thereof, which are useful as $5\text{-HT}_{1A}$ receptor antagonists.

2 Claims, No Drawings

SEROTONERGIC AGENTS

This is a continuation of application Ser. No. 10/218,251, filed on Aug. 14, 2002, now U.S. Pat. No. 6,586,436, which is a continuation of application Ser. No. 10/010,575, filed Nov. 13, 2001, now U.S. Pat. No. 6,469,007, which claims the benefit of provisional application Ser. No. 60/253,301, filed Nov. 28, 2000 and provisional application Ser. No. 60/297,814, filed Jun. 13, 2001, each of which is hereby incorporated by reference in their entirety.

FIELD OF THE INVENTION

This invention relates to novel piperazine derivatives, to their use and to pharmaceutical compositions containing them. The novel compounds are useful as $5\text{-HT}_{1A}$ binding agents, particularly as $5\text{-HT}_{1A}$ receptor antagonists.

BACKGROUND

U.S. Pat. No. 6,127,357 discloses compounds of the general formula (I):

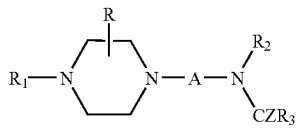

and pharmaceutically acceptable acid addition salts thereof wherein:
A is alkylene chain of 2 to 4 carbon atoms optionally substituted by one or more lower alkyl groups,
Z is oxygen or sulfur,
R is H or lower alkyl,
$R^1$ is a mono or bicyclic aryl or heteroaryl radical,
$R^2$ is a mono or bicyclic heteroaryl radical, and
$R^3$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^4R^5$ [where $R^4$ is hydrogen, lower alkyl, aryl or aryl(lower) alkyl and $R^5$ is hydrogen, lower alkyl, —CO(lower)alkyl, aryl, —Coaryl, aryl(lower)alkyl, cycloalkyl, or cycloalkyl-(lower)alkyl or $R^4$ and $R^5$ together with the nitrogen atom to which they are both attached represent a saturated hytrocyclic ring which may contain a further heteroatom], or a group of formula $OR^6$ [where $R^6$ is lower alkyl, cycloalkyl, cycloalkyl(lower)alkyl, aryl, aryl (lower)alkyl, heteroaryl or heteroaryl(lower)alkyl].

WO 97/03982 discloses compounds of the general formula (II):

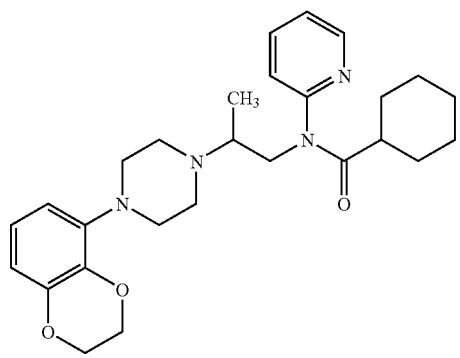

including enantiomers and the pharmaceutically acceptable acid addition salts thereof.

The compounds of formula (II) fall within the disclosure of U.S. Pat. No. 6,127,357 but are not specifically disclosed therein. Compounds of Formula II were taught to have potent $5\text{-HT}_{1A}$ antagonist activity in vivo when administered by the oral route.

DETAILED DESCRIPTION OF THE INVENTION

Novel compounds of the invention have the structural formula (III):

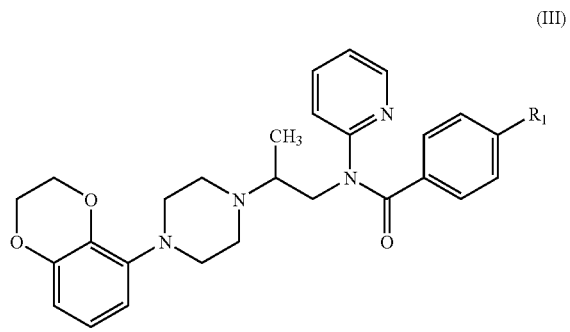

wherein $R_1$ is cyano, nitro, trifluoromethyl or halogen, or pharmaceutically acceptable acid addition salts thereof.

Halogen, as used herein, refers to chlorine, fluorine, bromine and iodine.

The compounds of Formula III contain an asymmetric carbon atom. Accordingly, they may exist in different stereoisomeric forms. In some preferred embodiments the R stereoisomer (Formula IIIa) is preferred.

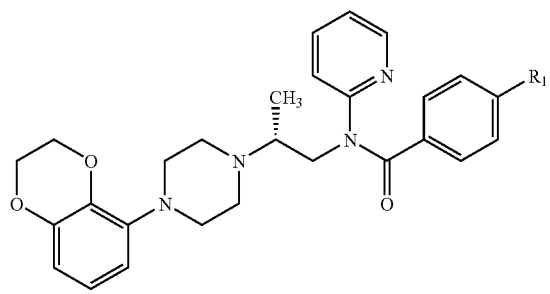

Formula IIIa

In accordance with some embodiments of the invention, the (R) stereoisomer is substantially free of the (S) stereoisomer. Substantially free, as used herein means that the compound is made up of a significantly greater proportion of its (R) stereoisomer than the (S) stereoisomer. In preferred embodiments the compound is made up of at least about 90% by weight of its (R) stereoisomer and about 10% by weight or less of its (S) stereoisomer. In other embodiments of the invention, the compound is made up of at least about 99% by weight of its (S) stereoisomer and about 1% by weight or less of the (R) stereoisomer. Preferred stereoisomers may be isolated from racemic mixtures by any method known to those skilled in the art, including high performance liquid chromatography (HPLC) and the formation and crystallization of chiral salts. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon*

Compounds (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The most preferred compounds of the invention are (R)-4-Cyano-N-{2-[4-(2,3-dihydro-benzo[1,4]dioxin-5-yl)-piperazin-1-yl]propyl}-N-pyridin-2-yl-benzamide; and pharmaceutically acceptable acid addition salts thereof.

The pharmaceutically acceptable salts are the acid addition salts which can be formed from a compound of the above general formula and a pharmaceutically acceptable acid such as, for example, benzoic, phosphoric, sulfuric, hydrochloric, hydrobromic, citric, maleic, malic, mandelic, mucic, nitric, fumaric, succinic, tartaric, acetic, lactic, pamoic, pantothenic, benzenesulfonic, or methanesulfonic acid. In some embodiments of the invention the preferred acid addition salt is hydrochloric acid.

The compounds of the present invention can be prepared by known methods from known starting materials which are available by conventional methods. For example the compounds may be prepared by the general methods disclosed in EP-A-0512755 and WO 97/03982.

Such disclosed methods include acylating an amine of formula (IV) with a known benzoyl chloride (V) or an alternative acylating derivative thereof. Examples of acylating derivatives include the acid anhydride, imidazolides (e.g. obtained form carbonyidiimidazole), or activated esters.

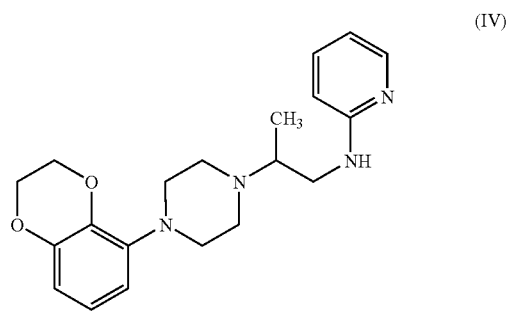

(IV)

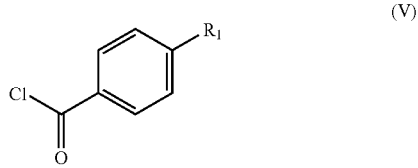

(V)

wherein $R_1$ is cyano, halogen, trifluoromethyl or nitro.

Novel compounds of the present invention are potent 5-$HT_{1A}$ binding agents which selectively binds to the 5-$HT_{1A}$ receptor. Furthermore, the novel compounds of the invention are 5-$HT_{1A}$ receptor antagonists when tested by standard pharmacological procedures.

In addition, the novel compounds of formula (III) are unique from previously disclosed 5$HT_{1A}$ receptor antagonists in that they possess a superior duration of action as a 5-$HT_{1A}$ receptor antagonist when administered in vivo.

EXAMPLES

The present invention is illustrated by reference to the following example. Those skilled in the art of organic synthesis may be aware of still other synthetic routes to the invention compound. The reagents and intermediates used herein are either commercially available or prepared according to standard literature procedures.

Example 1

(R)-4-Cyano-N-{2-[4-(2,3-Dihydro-Benzo[1,4]dioxin-5-yl)-Piperazin-1-yl]-Propyl}-N-Pyridin-2-yl-Benzamide A solution of {(R)-2-[4-(2,3-dihydrobenzo[1,4]dioxin-5-yl)piperazin-1-yl]propyl}-pyridin-2-ylamine (0.846 g, 2.38 mmol) in dichloromethane (20 mL) was treated at 0° C. with the dropwise addition of a dichloromethane solution of 4-cyanobenzoyl chloride (1.1 equivalents, 2.63 mmol in 5 mL). After stirring for 16 hours the mixture was poured onto hexane (100 mL) to precipitate the titled compound as its mono-hydrochloride salt (white solid, 1.2 g, 97% yield), which was recrystallized from dichloromethane/hexane.

MS (+) 484 (M+H)$^+$.

m.p. 239–240° C.

[α] 25/D=+56 (c=0.6, MeOH)

Elemental Analysis for: $C_{28}H_{29}N_5O_3$.1.0 HCl

Calculated: C, 64.67; H, 5.81; N, 13.47:

Found: C, 64.69; H, 5.93; N, 13.52:

In order to demonstrate the superior duration of action of the compounds of formula (III), Example 1 was compared to representative compounds of U.S. Pat. No. 6,127,357 and WO 97/03982.

Representative compounds of U.S. Pat. No. 6,127,357 possess a cyclohexylamide moiety and a 2-methoxyphenylpiperazine grouping. The most potent example of this general structure (and the most potent compound taught in U.S. Pat. No. 6,127,357) is compound A, described as "example 3" in U.S. Pat. No. 6,127,357. The only other class of compounds in U.S. Pat. No. 6,127,357 for which data are given is that which possess a cyclohexylamide moiety and a benzodioxinylpiperazine grouping ("Example 17" in U.S. Pat. No. 6,127,357). A small subset of this class of compounds is specifically claimed in WO97/03982, with the preferred compound being compound B ("example A1" in WO97/03982). Therefore, these two preferred examples from EP-A-0512755 and WO 97/03982 have been chosen as representatives for comparison to the compounds of formula (III).

Compound A

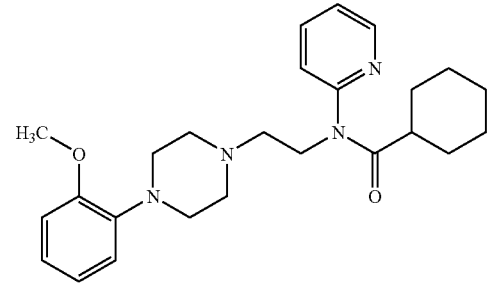

("Example 3" from U.S. Pat. No. 6,127,357)

Compound B

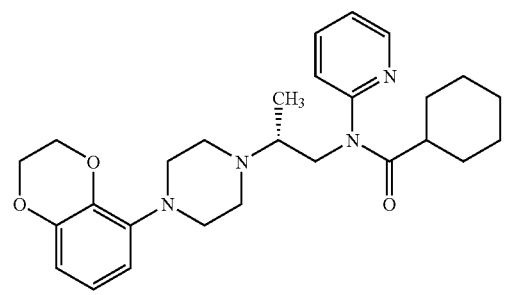

("Example A1" from WO 97/03982)

Example 2

Binding Profile

Compounds were tested for binding to cloned human 5-HT$_{1A}$ receptors stably transfected into CHO cells using [$^3$H]8-OH-DPAT as the 5-HT$_{1A}$ radioligand (according to general procedure described in J. Dunlop et al., *J. Pharmacol. Tox. Methods*, 40, 47–55 (1998)). As shown in Table 1, compounds of the present invention display high affinity for the 5HT$_{1A}$ receptor.

Example 3

IN VITRO Functional Activity

A clonal cell line stably transfected with the human 5-HT$_{1d}$ receptor was utilized to determine the intrinsic activity of compounds (according to the general procedure described in J. Dunlop et al., *J. Pharamcol. Tox. Methods*, 40, 47–55 (1998)). Data are provided in Table 1. As shown in Table 1, compounds of the present invention antagonized the ability of 10 nM 8-OH-DPAT to inhibit forskolin-stimulated cAMP production in a concentration-related fashion.

TABLE 1

| Compound | 5-HT$_{1A}$ Affinity Ki (nM) | 5-HT$_{1A}$ Antagonist Activity cAMP Assay ID$_{50}$ (nM) |
|---|---|---|
| Example 1 | 1.6 | 25 |
| Compound A | 0.96 | 7 |
| Compound B | 0.97 | 20 |

Example 4

IN VIVO Functional Activity

The ability of the compounds to function in vivo as 5-HT$_{1A}$ antagonists was assessed in rats using a Fixed Responding Model (D. Blackman, in "Operant Conditioning: An Experimental Analysis of Behavior", J. Butcher, ed., Methuen and Co., Ltd., London). In this model rats are trained to respond (lever pressing) under a fixed-ratio 30 schedule of food presentation in order to receive a food pellet reinforcer. Administration of the 5-HT$_{1A}$ agonist 8-OH-DPAT reduces the control response rate (assessed by administration of vehicle placebo). The 5-HT$_{1A}$ antagonist activity of a test compound is determined by measuring its ability to antagonize this agonist-induced decrease in response rate. A full antagonist effect is considered one in which the test compound completely reverses the agonist-induced response rate, returning it to control levels. The data given in Table 2 demonstrate that a 1 mg/kg dose of the compound of Example 1 completely reverses the decrease in response rate induced by administration of a 0.3 mg/kg dose of 8-OH-DPAT. Thus, compounds of the present invention function as 5-HT$_{1A}$ antagonists in vivo.

TABLE 2

Response Rate (responses/second)

| Vehicle (Control) | 8-OH-DPAT (0.3 mg/kg sc) | 8-OH-DPAT (0.3 mg/kg sc) + Example 1 (1 mg/kg sc) |
|---|---|---|
| 2.4 ± 0.5 | 0.5 ± 0.2 | 2.5 ± 0.2 |

Example 5

Duration of Action IN VIVO

The duration of action in the Fixed Responding Model was assessed by pre-treating animals with test compound and then challenging with a 0.3 mg/kg dose of the 5-HT$_{1A}$ agonist 8-OH-DPAT at various time intervals after the administration of test compound. All drug and vehicle administrations were made by the subcutaneous route. Doses of the test compounds selected for comparison were those which caused a ten-fold shift in the 8-OH-DPAT dose-response curve when administered 30 minutes prior to agonist. The doses selected for the duration of action comparison are listed in Table 3.

TABLE 3

| Test Compound | Dose Which Shifts Agonist Dose-response Curve by 10-fold (mg/kg, sc) |
|---|---|
| Compound A (FIG. 1) | 0.03 |
| Compound B (FIG. 1) | 0.1 |
| Example 1 | 1.0 |

Data are presented for pre-treatment of the animals with test compound at 0.5 hours, 2 hours, and 4 hours prior to administration of a 0.3 mg/kg dose of 8-OH-DPAT. Results are normalized to control values, with 100% being the control response rate observed when vehicle is administered rather than the agonist 8-OH-DPAT.

TABLE 4

| | % Response Rate | | |
|---|---|---|---|
| Compound | 0.5 hour pretreatment | 2 hour pretreatment | 4 hour pretreatment |
| Compound A + 8-OH-DPAT | 90 ± 3 | 55 ± 28 | 41 ± 26 |
| Control + 8-OH-DPAT | 23 ± 9 | 3 ± 1 | 3 ± 1 |
| Compound B + 8-OH-DPAT | 100 ± 11 | 71 ± 12 | 27 ± 14 |
| Control + 8-OH-DPAT | 21 ± 9 | 42 ± 6 | 42 ± 6 |
| Example 1 + 8-OH-DPAT | 100 ± 7 | 118 ± 13 | 99 ± 16 |
| Control + 8-OH-DPAT | 29 ± 6 | 35 ± 10 | 35 ± 10 |

As can be seen from Table 4, all three test compounds (Compound A, B and Example 1) completely antagonize the agonist-induced decrease in responding 30 minutes after their administration, returning the response rate to control levels. However, when agonist is given 2 hours following test drug administration (Column 3), the 5-HT$_{1A}$ antagonist effects of compounds A and B no longer return the response rate to control levels while Example 1 still displays complete 5-HT$_{1A}$ antagonist effects. By four hours post-administration (Column 4), the 5-HT$_{1A}$ antagonist effects of Compounds A and B are completely lost, while Example 1 continues to provide complete antagonism of the agonist-induced decrease in response rate. Thus, the duration of action of Example 1 is longer than 4 hours, while those of Compounds A and B are somewhere between 30 minutes and 2 hours.

The increased duration of action of the novel compounds of the present invention, compared to that of the classes of compounds disclosed in U.S. Pat. No. 6,127,357 and WO 97/03982 is particularly advantageous in that a smaller number of doses of the compound can be administered to produce a similar therapeutic effect.

Compounds of the present invention may be used to treat a subject suffering from CNS disorders such as schizophrenia, (and other psychotic disorders such as paranoia and mano-depressive illness), Parkinson's disease and other motor disorders, anxiety (e.g. generalized anxiety disorders, panic attacks, and obsessive compulsive disorders), depression (such as by the potentiation of serotonin reuptake inhibitors and serotonin norepinephrine reuptake inhibitors), Tourette's syndrome, migraine, autism, attention deficit disorders and hyperactivity disorders. Compounds of the present invention may also be useful for the treatment of sleep disorders, social phobias, pain, thermoregulatory disorders, endocrine disorders, urinary incontinence, vasospasm, stroke, eating disorders such as for example obesity, anorexia and bulimia, sexual dysfunction, and the treatment of alcohol, drug and nicotine withdrawal.

Compounds of the present invention are also useful for the treatment of cognitive dysfunction. Thus, compounds of the present invention may be useful for the treatment of cognitive dysfunction associated with mild cognitive impairment (MCI)) Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

"Provided", as used herein with respect to providing a compound or substance covered by this invention, means either directly administering such a compound or substance, or administering a prodrug, derivative, or analog which will form an equivalent amount of the compound or substance within the body. Prodrugs can be prepared such as described in *Design of Prodrugs,* Bundgaard, H. ed., (Elsevier, N.Y. 1985); *Prodrugs as Novel Drug Delivery Systems,* Higuchi, T and Stella, V. eds, (American Chemical Society, Washington, D.C. 1975); *Design of Biopharmaceutical Properties through Prodrugs and Analoqs,* Roche, E. ed., (American Pharmaceutical Association Academy of Pharmaceutical Sciences, Washington, D.C., 1977); and Metabolic Considerations in Prodrug Design, Balant, L. P. and Doelker, E. in *Burger's Medicinal Chemistry and Drug Discovery,* Fifth Edition, Wolff, M., ed, Volume 1, pages 949–982, (John Wiley & Sons, Inc. 1995).

The compounds of the present invention may be administered orally or parentally, neat or in combination with conventional pharmaceutical carriers. Applicable solid carriers can include one or more substances which may also act as flavoring agents, lubricants, solubilizers, suspending agents, fillers, glidants, compression aids, binders, tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions which are sterile solutions or suspensions can be utilized by, for example, intramuscular, intraperitoneal or subcutaneous injection. Sterile solutions can also be administered intravenously. Oral administration may be either in liquid or solid composition form. Preferably, the pharmaceutical compositions containing the present compounds are in unit dosage form, e.g., as tablets or capsules. In such form, the composition is sub-divided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a capsule or tablet itself, or it can be the appropriate number of any such compositions in package form. The therapeutically effective dosage to be used may be varied or adjusted by the physician and generally ranges from 0.5 mg to 750 mg, according to the specific condition(s) being treated and the size, age and response pattern of the patient.

The present invention may be embodied in other specific forms without departing from the spirit and essential attributes thereof and accordingly, reference should be made to the appended claims, rather than to the foregoing specification, as indicating the scope of the invention.

What is claimed is:

1. A method for treating cognitive impairment in an Alzheimer's disease patient, the method comprising providing to the patient a therapeutically effective amount of a compound of formula (III):

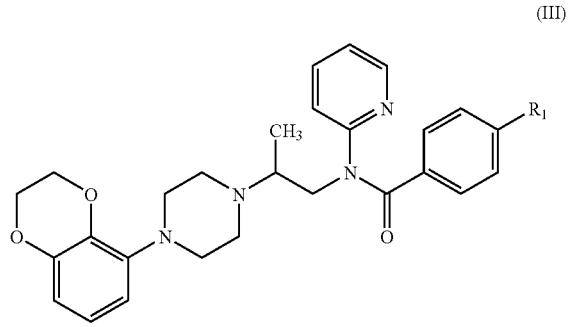

(III)

wherein $R_1$ is cyano, nitro, trifluoromethyl or halogen, or pharmaceutically acceptable acid addition salts thereof.

2. The method of claim 1, wherein the compound is (R)-4-cyano-N-{2-[4-(2,3-dihydro-benzo[1,4]dioxin-5-yl)piperazine-1-yl]-propyl}-N-pyridin-2-yl-benzamide.

* * * * *